(12) United States Patent
Dalhoff et al.

(10) Patent No.: US 10,561,347 B2
(45) Date of Patent: Feb. 18, 2020

(54) METHOD AND DEVICE FOR EXAMINING THE FACULTY OF HEARING

(71) Applicant: EBERHALD KARLS UNIVERSITAT TUBINGEN, Tubingen (DE)

(72) Inventors: Ernst Dalhoff, Rottenburg (DE); Dennis Zelle, Tubingen (DE)

(73) Assignee: Eberhard Karls Universitat Tubingen, Tübingen (DE)

(*) Notice: Subject to any disclaimer, the term of this patent is extended or adjusted under 35 U.S.C. 154(b) by 304 days.

(21) Appl. No.: 15/320,474

(22) PCT Filed: Jun. 19, 2015

(86) PCT No.: PCT/EP2015/001246
§ 371 (c)(1),
(2) Date: Dec. 20, 2016

(87) PCT Pub. No.: WO2015/192969
PCT Pub. Date: Dec. 23, 2015

(65) Prior Publication Data
US 2017/0150909 A1    Jun. 1, 2017

(30) Foreign Application Priority Data
Jun. 20, 2014 (DE) .......... 10 2014 108 663

(51) Int. Cl.
*A61B 5/12* (2006.01)
*A61B 5/00* (2006.01)

(52) U.S. Cl.
CPC ............ *A61B 5/125* (2013.01); *A61B 5/6817* (2013.01)

(58) Field of Classification Search
CPC ...................................... A61B 5/121
See application file for complete search history.

(56) References Cited

U.S. PATENT DOCUMENTS 5,267,571 A * 12/1993 Zurek ............... A61B 5/12
                                                        600/559
5,413,114 A *  5/1995 Zurek ............... A61B 5/12
                                                        600/559
(Continued)

FOREIGN PATENT DOCUMENTS

DE          69738629 T2    5/2009
DE       102011121686 A1    6/2013
(Continued)

OTHER PUBLICATIONS

Ernst Dalhoff et al: "Two-source interference as the major reason for auditory-threshold estimation error based on DPOAE input-output functions in normal-hearing subjects", Hearing Research, vol. 296, Feb. 1, 2013, p. 67-82. (Year: 2012).*
(Continued)

*Primary Examiner* — Daniel L Cerioni
*Assistant Examiner* — Raymond P Dulman
(74) *Attorney, Agent, or Firm* — Dinsmore & Shohl LLP

(57) ABSTRACT

In a method for examining the faculty of hearing for at least one ear of a mammal, in which growth curves are determined on the basis of the measurement of DPOAE's evoked by pairs of excitation signals (f1, f2) for different excitation frequencies f2, the ear is presented with first excitation signals with a first excitation frequency f1 and a first noise level L1 and secondary excitation signals with a second excitation frequency f2 and a second noise level L2. Pulse pairs with a first pulse of the first excitation signal and a second pulse of the second excitation signal are presented in the ear, and the DPOAE's evoked thereby are captured and evaluated. A set of at least two different pulse pairs with different second excitation frequencies f2 is presented in one block that is repeated several times during a measuring period.

23 Claims, 7 Drawing Sheets

(56) References Cited

U.S. PATENT DOCUMENTS

| | | | | |
|---|---|---|---|---|
| 5,792,073 A * | 8/1998 | Keefe | ............... | A61B 5/121 600/559 |
| 5,885,225 A * | 3/1999 | Keefe | ............... | A61B 5/121 600/559 |
| 7,333,619 B2 * | 2/2008 | Causevic | ......... | A61B 5/04845 381/94.1 |
| 2003/0185408 A1 * | 10/2003 | Causevic | ......... | A61B 5/04845 381/94.1 |
| 2014/0114209 A1 | 4/2014 | Lodwig | | |

FOREIGN PATENT DOCUMENTS

| | | |
|---|---|---|
| EP | 1027863 A1 | 8/2000 |
| EP | 2053877 A1 | 4/2009 |

OTHER PUBLICATIONS

Dhar Sumitrajit et al: "The effect of stimulus-frequency ratio on distortion product otoacoustic emission components", The Journal of the Acoustical Society of America, American Institute of Physics for the Acoustical Society of America, vol. 11 7, No. 6, Jun. 1, 2005 (Jun. 1, 2005), (Year: 2005).*

Whitehead Ml et al: "Measurement of otoacoustic emissions for hearing assessment", IEEE Engineering in Medicine and Biology Magazine, IEEE Service Center, vol. 13, No. 2, Apr. 1, 1994 (Apr. 1, 1994), pp. 210-226 (Year: 1994).*

Dalhoff, E. et al., Schall und Geschwindigkeits-DPOAE; Technologie, Methodik und Perspektiven, HNO; Deutsche Gesellschaft für Hals-Nasen-Ohren-Heilkunde, DE, Bd. 58, Nr. 6, 2010, Seiten 543-555.

Zelle, D. et al., Extraction of otoacoustic distortion product sources using pulse basis functions, The Journal of the Acoustical Society of America, 134(1): ELL64-EL69, 2013.

Salata, et al., Distortion-product otoacoustic emissions hearing-screening in high-risk newborns, Otolaryngology and head and neck surgery, 118(1): 37-43, 1998.

Mills, D. M. "Interpretation of distortion product otoacoustic emission measurements", The Journal of the Acoustical Society of America 102 (1), pp. 413-429, Jul. 1997.

Whitehead, M. L. et al. "Dependence of distortion-product otoacoustic emissions on primary levels in normal and impaired ears. II. Asymmetry in L1, L2-space", The Journal of the Acoustical Society of America 97 (4), pp. 2359-2377, Apr. 1995.

Zelle, D. et al: "Level dependence of the nonlinear-distortion component of distortion-product otoacoustic emissions in humans", J. Acoustic Soc. Am. 138 (6), pp. 3475-3490, Dec. 2015.

* cited by examiner

METHOD AND DEVICE FOR EXAMINING THE FACULTY OF HEARING

FIELD OF THE INVENTION

The present invention relates to a method for examining the faculty of hearing for at least one ear of a mammal, in which growth curves are determined on the basis of the measurement of DPOAE's (distortion products of otoacoustic emissions), evoked by pairs of excitation signals (f1, f2), for different excitation frequencies f2, comprising the steps:

First excitation signals having a first excitation frequency f1 and a first sound level L1 and second excitation signals having a second excitation frequency f2 and a second sound level L2 are presented in the ear; and Pulse pairs comprising a first pulse of the first excitation signal and a second pulse of the second excitation signal are presented in the ear, and the DPOAE's evoked thereby are detected and evaluated.

BACKGROUND OF THE INVENTION

The generation process of the DPOAE's and the previously used measurement and evaluation methods are described in Dalhoff et al. "Schall- and Geschwindigkeits-DPOAE" [Sound and Velocity DPOAE's] in HNO [ENT] 2010, 58: 543-555, for example. Included there are additional proofs, to which reference is made expressly.

The known methods are used for objectively and quantitatively determining the sound processing in a mammal's ear and thus for examining and subsequently evaluating the faculty of hearing. The methods are based upon the measurement of distortion products of otoacoustic emissions (DPOAE's) that are generated by pairs of excitation signals.

According to EP 2 053 877 A1 and DE 199 05 743 A1, the measurement results can also be used to adjust hearing aids.

The auditory system can be regarded as a chain of processing blocks, which are gone through before the more complex auditory perception takes place in the cortex. The first blocks are the outer ear (auricle and acoustic meatus), the middle ear (auditory ossicles with the base plate as boundary to the fluids of the inner ear), and the fluid-filled inner ear. These three blocks are also called the periphery; several neural processing nodes follow these blocks, before the signals arrive in the cortex. The inner ear comprises the cochlea, which constitutes the receptor field for the auditory perception and in which sounds are decomposed into their individual frequencies in a manner similar to a Fourier analysis.

Most hearing impairments develop in the inner ear. This also includes the age-related hearing loss, which on average results in a 35 dB hearing loss in men 60 to 70 years old and in a 25 dB hearing loss in women of the same age group at frequencies starting at 4 kHz.

This age-related hearing loss is dominated by an impairment of the so-called cochlear amplifier (the mechanical amplification of the traveling wave in the cochlea) in the inner ear, which amplifier in the healthy condition achieves an amplification of the vibration in the inner ear by the factor 300 to 1000 through a complex interplay of electro-mechano-biochemical mechanisms, before the vibrations are converted into neural signals by the inner hair cells.

The key element of the cochlear amplifier is constituted by the outer hair cells, which in principle act like piezo actuators. In contrast to most impairments of the middle ear, impairments of the cochlear amplifier cannot yet be treated successfully today.

The condition of the middle ear can generally be detected sufficiently by means of tympanometry. The condition of the entire auditory system is examined subjectively by pure-tone audiometry and speech comprehension tests, and objectively by diversion of neural excitation.

In case of a hearing loss, if an impairment of the middle ear components is excluded, the decision between a neural and cochlear impairment remains. The measurement of otoacoustic emissions (OAE's) is used for this purpose. OAE's are active, acoustic emissions of the ear that retrogradely, i.e., opposite to the direction of sound perception, arrive via the path through the auditory ossicles and the eardrum in the acoustic meatus and can be recorded there by means of highly sensitive measuring microphones.

Two different types of OAE's are distinguished, viz., the spontaneous OAE's and the evoked OAE's, which are evoked by acoustic stimuli. The spontaneous OAE's (SOAE's) occur in 35 to 50% of healthy ears and are not audible to the producer himself, and they do not have any substantial clinical significance.

The evoked OAE's (EOAE's) occur during or shortly after an acoustic stimulation of the ear. Depending upon the form of the acoustic stimulus, different subgroups of evoked OAE's are distinguished, which, in particular, include the transitory evoked OAE's (TEOAE's), which are detectable after a short acoustic stimulus, and the distortion product otoacoustic emissions (DPOAE's), which are generated by two simultaneously applied sinusoidal tones (f1 and f2).

The method according to the invention for determining the condition of the cochlea is based upon the measurement of the DPOAE's, i.e., the subgroup of the OAE's that has been researched particularly intensively.

DPOAE's are byproducts of a healthy, active inner ear amplifier, which amplifies the vibrations generated in the inner ear by an acoustic stimulus by a factor of 100 to 1000 in humans and other mammals, before the conversion into neural signals occurs. For this purpose, the cochlear amplifier uses external energy that must be provided by the metabolism.

DPOAE's are generated by simultaneous stimulation with two primary tones f1 and f2 with excitation levels L1 and L2. In this case, the two primary tones f1 and f2 are so-called "pure tones," which contain precisely one frequency only. In accordance with the general Fourier relation between the time and frequency domain, these tones would therefore have to continue infinitely, since the spectrum would otherwise widen. Since this infinitely long continuation cannot be realized, the person skilled in the art considers these to be tones that are presented for so long as their spectrum is sharp. The marked non-linearity in the characteristic curve of the cochlear amplifier results in the generation of distortion products, which are partially transmitted retrogradely back into the acoustic meatus and can be measured there using suitable instruments. In the process, a certain distortion product is evaluated, which is preferably at the frequency $fdp=2f1-f2$. Its amplitude allows conclusions regarding the condition of the cochlear amplifier, which conclusions are useful in the general clinical practice, e.g., in the screening of newborns for hearing impairments requiring treatment.

Generally, the amplitude of the DPOAE is extracted from the spectrum of the measured signal using Fourier transformation. Since the DPOAE's have a very low sound level, which can be considerably below the hearing threshold, averaging must be performed long enough in order to obtain a certain signal-to-noise ratio and thus reliable diagnostic information.

In diagnostic applications, the frequency ratio f2/f1 is preferably held constant, because each species has a frequency ratio where the DPOAE is strongest and can thus be measured most easily. In humans, this ratio is 1.2 and thus corresponds to a minor third.

The main part of the DPOAE signal is produced in the inner ear at a location where f2 is actually mapped. This is because the traveling wave of f2 is there at a maximum, and the traveling wave of the f1 tone is also already very strong at that location. On the other hand, at a further apical location of the maximum of the f1 traveling wave, the f2 wave is already completely collapsed. The f2 mapping location is therefore the location where both tones are relatively strong and are thus processed simultaneously by the strongly non-linear characteristic curves of the ion channels of the outer hair cells.

The person skilled in the art, as well as the ENT physician, therefore always associates a DPOAE event with the f2 frequency, i.e., compares a DPOAE stimulated with f2=3 kHz with the audiogram at 3 kHz, even though the frequency of the DPOAE itself is below that by, fairly precisely, two thirds.

If several such DPOAE's are measured at a frequency f2 and at different sound levels L2 and combined in a so-called growth function, more precise information about the function of the cochlear amplifier in the inner ear results. For each frequency f2, the so-called threshold value can then be determined using the growth curve, which threshold value is the lowest excitation level L2 at which the DPOAE still reaches a given minimum signal-to-noise ratio. This threshold value cannot be measured, since the noise measured along with it is finite, but must be determined by extrapolation.

In order to obtain diagnostic information across the entire frequency domain, 6 to 8 growth functions are therefore typically measured sequentially.

The growth curves determined in this way and the threshold values extrapolated from them can then be used as the basis for improved diagnostics and to adjust hearing aids, because the extrapolated threshold values can be regarded as a direct statement about the hearing loss; see DE 199 05 743 A1 mentioned above.

In this case, the excitation of the DPOAE's can be carried out both by continuous tones and by pulsed tones. As already mentioned above, continuous tones in this respect refer to tones that are presented for as long a time as their spectrum is sharp. In case of the pulsed DPOAE's, f1 is fed in as a continuous tone or in a pulsed manner, and f2 is fed in in a pulsed manner, wherein the ratio of L2 to L1 is adjusted to a certain range, and L2 is then changed gradually. According to the general Fourier relation between the time and frequency domain, the pulsed tones are tones the spectrum of which is widened as a result of the shortness of the pulse. If one of the tones, such as the aforementioned tone f1, is presented as a continuous tone, this means that the tone f2 fed in in a pulsed manner passes through an on-and-off process while the tone f1 continues.

By measuring the growth functions using pulsed DPOAE's, certain artifacts, known as the "two-source problem" in continuous tone DPOAE's, are prevented.

The method is based upon two key components: 1) Extraction of the so-called non-linear components of the DPOAE's using pulsed stimulation and temporal isolation; 2) Measurement of the growth functions of pulsed DPOAE's using the extrapolation method of Boege & Janssen, with the important modification of the "high-level saturation correction." Both methods are described in Dalhoff et al., "Two-source interference as the major reason for auditory-threshold estimation error based on DPOAE input-output functions in normal-hearing subjects," in Hearing Research 296 (2013), pp. 67-82.

The present invention addresses the improvement of this method in detail.

The known method has a disadvantage that prevents it from being used in the ENT routine. The estimation of the auditory threshold at only one frequency takes about 480 s with the known methods, wherein obvious measures to reduce this measurement period to 96 s were discussed. If the usual set of seven frequencies for the clinical description of the faculty of hearing is to be tested, a measurement period of 11 min results even for those with normal hearing.

A substantial disadvantage of the known method thus consists in the fact that it is very slow, and that it was therefore considered so far to not be usable clinically—in particular, because it is far too lengthy for examining the hearing-impaired. Moreover, the achievable accuracy in the determination of the growth curves and the extrapolated threshold values is often not satisfactory.

This is the point from which the further developed method according to the invention of fast pulse distortion product otoacoustic emissions (pulse DPOAE's) proceeds, the task of which invention is to create a quickly performed and nonetheless precise method of the aforementioned type.

SUMMARY OF THE INVENTION

According to the invention, this aim is achieved in the aforementioned method by a set of at least two different pulse pairs (each pulse pair with an excitation frequency of f1 and f2) with different second excitation frequencies f2 (and as a consequence, also different first excitation frequencies f1) presented in a block that is repeated multiple times during a measurement period. An example of two different pulse pairs of a block is a first pulse pair with an excitation frequency f2 of 1.5 kHz and an excitation frequency f1 of 1.25 kHz and a second pulse pair with an excitation frequency f2 of 4 kHz and an excitation frequency f1 of 3.33 kHz. In this case, the excitation frequencies f2 and f1 of a pulse pair are preferably related via a frequency ratio f2/f1=1.2. Deviatiing from this frequency ratio f2/f1 of 1.2, this frequency ratio can, however, also be specified to be another suitable value between 1.15 and 1.35. However, since in the present case, the focus is on the threshold value determination, a frequency ratio f2/f1 of 1.2 or 1.22 is advantageous, because the frequency ratio is barely dependent upon the frequency in the case of low excitation sound pressures, according to the current state of knowledge. When f2 pulse pairs are discussed below, this always refers to f1-f2 pulse pairs in which the frequency f1 is determined via a defined frequency ratio from f2, and when discussing the excitation level L2 in this context, it is assumed that the level L1 of the f1 pulse is calculated from L2 according to a predefined rule.

Compared to continuous DPOAE's, pulsed DPOAE's first have the serious disadvantage that the measurement at a frequency/sound level combination generally shows a low time utilization and thus a correspondingly low signal-to-noise ratio in the same measurement period, which is why the use of pulse pairs seems to even prolong the measurement period at first glance.

This advantage is, however, significantly reduced according to the invention by combining several measurements in the time-frequency space, i.e., presenting them alternately at staggered intervals. In this way, seven frequencies can be stimulated and analyzed at staggered intervals within one block, for example.

The aim upon which the invention is based is achieved completely in this manner.

According to the invention, an acceleration of the method is achieved using parallel and adaptive stimulation and analysis steps. With the new method, growth curves for 5 frequencies f2 were generally measured in 2.5 min in current tests by the inventors. Estimates show that growth curves for all seven frequencies can be measured with the method in 2 min.

The inventors also have designed a threshold value approximation method that aims at adaptively measuring as few points of the growth function as possible—preferably 3 or 4—during an individual measurement, in order to save time without sacrificing accuracy.

For this purpose, the excitation levels L2 must be selected according to the patient and the frequency-dependent condition of the patient's hearing.

Moreover, with the new method, the inventors have shown that the best way so far is, in their opinion, to be able to reliably suppress artifacts caused by physiological processes (generated, for example, by heart beats, breathing, swallowing, coughing, or reflexes of the muscle in the middle ear) in a nevertheless quick measurement method.

The inventors could thereby show for the first time that a threshold value estimation of the cochlear condition with a standard deviation of only 3 to 4 dB is possible with the new method, wherein individual threshold value estimations do not show errors of more than 10 dB.

Whereas the generally six to eight growth curves were previously measured sequentially, these measurements are now taken in combination according to the invention.

In principle, the disadvantage that pulsed signals do not use the entire time of a measurement block, and thus lose SNR, is eliminated by the pulse combination method.

For this purpose, the signal-to-noise ratio of the spectrum is averaged during the current measurement based upon the already registered signal blocks. As soon as the desired signal-to-noise ratio is reached, the measurement is discontinued. Since the background noise varies greatly over time as a result of physiological processes, such as heart beats, breathing, and swallowing, a noise evaluation of each individual block is performed during the measurement, and individual blocks are discarded if the noise exceeds a certain, empirically determined threshold value.

The invention further relates to a device for performing the new method, which device comprises at least one ear probe to be placed in/on the ear or two miniature loudspeakers and one receiver (microphone), wherein each miniature loudspeaker is designed for the presentation of a first excitation signal with a first excitation frequency f1 and a first sound level L1 and/or a second excitation signal with a second excitation frequency f2 and a second sound level L2, and wherein the receiver is designed for detecting and transmitting a DPOAE evoked by the first and second excitation signals, wherein a computer unit is furthermore provided, which is programmed and configured to present a set of at least two pulse pairs with different second excitation frequencies f2 in a block that is passed through repeatedly multiple times during a measurement period, so that the pulse pairs of a set are presented in combination, i.e., alternately, at staggered intervals.

The first and the second pulses in a pulse pair are presented at the same time or at a small temporal offset. Usually, the f1 pulse is turned on 3-10 ms earlier and turned off 3-10 ms later depending upon the frequency, so that the f1 excitation reaches a steady state for a short period of time during the presentation of the f2 pulse. In this respect, larger time offsets always mean a possible loss of time. This can, however, also be done, for the greatest possible time savings, with two identical or similar short pulses for f1 and f2 that are temporally offset such that both excitations take place simultaneously at the most diagnostically useful mapping location for f2 in the cochlea. Then, the f1 pulse is turned on approx. 0.1-3 ms later, since its transit time to the mapping location of frequency f2, which is located closer basally (in the direction of the base plate), is shorter than that of the f2 wave. If this setting is optimally selected, an effect by the afferent-efferent feedback loop of the medial olivocochlear reflex does not yet take place.

The excitation frequency f1 is determined from a specified excitation frequency f2 according to a specified ratio between f1 and f2, as described already.

As already described, the ratio is preferably f2/f1=1.2 because a DPOAE as strong as possible is achieved at this ratio, based upon experience. The ratio can be easily adjusted for further optimization depending upon f2 and L2; see, for example, Johnson et al., "Influence of primary-level and primary-frequency ratios on human distortion product otoacoustic emissions," in J. Acoust. Soc. Am. 119, 2006, pp. 418-428.

The first and second excitation frequencies are preferably in the range of 250 Hz to 10 kHz.

The duration of the first and the second pulses in a pulse pair is preferably 2 to 20 ms. In the process, the pulse with excitation frequency f1 of a pulse pair starts before the pulse with excitation frequency f2 starts, and ends after the pulse with excitation frequency f2 has ended, i.e., the pulse with excitation frequency f1 is longer than the pulse of excitation frequency f2 of a pulse pair. It goes without saying that these relations can also be completely reversed, viz., that the pulse with excitation frequency f2 start before the pulse with excitation frequency f1 starts, and that the pulse with excitation frequency f1 end before the pulse with excitation frequency f2 ends, so that the pulse of excitation frequency f2 is longer than the pulse of excitation frequency f1 of a pulse pair. In this respect, the inventors consider the so-called full width half maximum ($T_{HB}$ or $T_{FWHM}$) as the pulse length. For this pulse length, the time is determined starting from when the cosine-shaped rising edge rises to half the steady-state value until the corresponding point in time in the falling edge.

This pulse length results from the preferred pulse shape, according to which the pulses have a cosine-shaped rise of a length of 0.1 to 4 ms, a steady-state with the level L2 or L1, which is 2 to 12 ms long, followed by another cosine-shaped section.

The total length of a pulse is measured in a preferred embodiment such that it reaches its full amplitude during the response of the first contribution to the DPOAE, i.e., the non-linear contribution, starts, but is already fading when the response of the second contribution to the DPOAE starts.

In this way, two objectives are achieved, viz., to use as little time as possible for the measurement of the first (non-linear) contribution of a DPOAE, and to clearly separate it from the second contribution. Possible pulse shapes are described in Whitehead et al., "Visualization of the onset of distortion-product otoacoustic emissions, and measurement of their latency," in J. Acoust. Soc. Am. 100 (3), 1996, pp. 1663-1679, and Zelle et al., "Extraction of otoacoustic distortion product sources using pulse basis functions," in Acoust. Soc. Am. 134, 2013, pp. EL64-69.

In order to effectively suppress the primary tones (f1 and f2), the primary tone phase variation method by Whitehead et al., 1996, l.c., is preferably used in addition to conventional filter methods.

As a whole, it is preferred if, in a block, the start of a pulse pair follows the start of the pulse pair immediately preceding it in the block, with a time lag T ($T_{SLOT}$ or $T_S$), wherein T is generally at least the length of the preceding pulse, i.e., >10 ms. This measurement period reserved for a pulse pair in a block is also called a slot below. It must be noted in this respect that slots do not overlap, but that one slot follows the other, when the preceding slot has ended. As explained above, the slot length ($T_S$) is more than 10 ms in this case.

In this respect, it is advantageous that, in this way, the second pulse pair is not presented until the DPOAE evoked by the first pulse pair has faded enough (to approx. 1 to 10% of the initial value) so that no marked disturbances in the measurement of the levels (Ldp) of the individual DPOAE's result, which DPOAE's have only a very low sound pressure level (SPL) compared to the sound levels L1 and L2 of the excitation pulses. In addition, the increased time lag between the presentation of pulse pairs with the same excitation frequencies f1 and f2 allows for a sufficient recovery time for the DPOAE evoked in the preceding measurement block to completely fade.

If, for example, a time lag T or a slot length Ts=40 ms is selected for each pulse pair in a block in a measurement with four pulse pairs, a recovery time of 3×40 ms, i.e., 120 ms, results for each DPOAE of an excitation frequency f2, before the measurement is repeated at the same excitation frequency f2. Within a total block time ($T_B$) of 160 ms (4×40 ms=4×$T_S$) resulting in this way, DPOAE's for four second excitation frequencies f2 can thus be measured in this example, without the excitation frequencies mutually or as a result of a fading time that is too short influencing one another. In this example, the block thus has four slots with a slot length $T_S$ of 40 ms each, wherein the current configuration of the slots with pulse pairs of different second excitation frequencies f2 is called a panel.

The danger of the pulse pairs mutually influencing one another, as well as the DPOAE's evoked by them in a block, exists because, in a simultaneous presentation of stimuli, the traveling waves can drive the non-linear transmission in the inner ear into saturation, which is called suppression or masking. The measurement, in particular, of simultaneously presented higher frequencies is falsified thereby.

It is furthermore preferred, if, in a block, the second excitation frequencies f2 of two pulse pairs immediately following one another, i.e., in two consecutive slots, are at least one octave apart. In the process, the first excitation frequencies f1 are selected as described.

It is also advantageous in this respect that no marked disturbances in the measurement of the individual DPOAE's result, because according to the invention, it is provided that the frequency separation between the excitation frequencies f1, f2, and therefore also the frequencies fdp of the respectively evoked DPOAE's, is sufficiently large. It has been shown that a frequency separation of an octave is sufficient.

A preferred set (preferred panel) consists of the excitation frequencies f2=1 kHz, f2=3 kHz, f2=1.5 kHz, and f2=6 kHz, which are presented repeatedly as a panel in a block in this order. A panel is to be regarded as the frequency time pattern of the excitation frequencies in a block.

Another preferred set (preferred panel) consists of the excitation frequencies f2=2 kHz, f2=4 kHz, f2=1.5 kHz, and f2=3 kHz, which are presented repeatedly as a panel in a block in this order. Since twice as much time is usually required for the measurement at 1 kHz to reach a certain signal-to-noise ratio than for the measurement at the other (higher) frequencies, a shorter measurement period is usually required for this set until a desired signal-to-noise ratio (SNR) is reached.

It is generally preferred if the measured sound levels Ldp of the DPOAE's are averaged for pulse pairs of the same first and second excitation frequencies f1, f2 during the measurement period.

In this respect, it is advantageous that the measurements with the blocks of the set of pulse pairs are repeated over a certain period of time—the measurement period—because the SNR is improved if the DPOAE's for pulse pairs of the same excitation frequencies f1, f2 are averaged.

It is further preferred if the or each block of pulse pairs is presented during a block time $T_B$ that is selected such that a time lag of 30 to 100 ms—preferably of at least 70 ms—lies between the start of a first and a following pulse pair with the same excitation frequency f2. As already explained, the block time $T_B$ is the sum of the slot lengths $T_S$ of a block.

According to the knowledge of the inventors, this time lag is sufficient for a pulse to have faded enough when it is repeated.

It is generally preferred if, at the beginning of a measurement, it is checked whether the frequency fdp of one of the DPOAE's interferes with a spontaneous emission (SOAE).

In this respect, it is advantageous that artifacts and sources of interferences are already detected at the beginning of the measurement. If this is the case, either the block time $T_B$ or the time period $T_S$ for one or all slots can be adjusted such that the fading time of the DPOAE is extended far enough that its level ends up below a certain threshold value before the next pulse pair is presented, or that the frequency f2 is moved in order to create a minimum separation from the SOAE.

It is preferred in this respect if, at the beginning of a measurement for a pulse pair with a first excitation frequency f1 and a first sound level L1 and a second excitation frequency f2 and a second sound level L2, a DPOAE is measured, and, in case a DPOAE cannot be measured, the sound level L2 (and the sound level L1) is increased incrementally until either the maximum sound level L2 (L1) that can be output is reached or a DPOAE is measured. In this simple manner, the presence of interfering SOAE's can be detected, and possibly compensated for.

It is further preferred if, within a block, the sound levels of the pulse pairs are selected to be similar, since the danger of mutual suppression increases with increasing level difference.

In a simple embodiment, a fixed threshold value, which is between 5 and 15 dB in a preferred embodiment, can be defined for the maximum level difference between the L2 sound levels of, for example, four pulse pairs in a block.

On the one hand, it is preferred if the sequence of pulse pairs and the time lag between two consecutive pulse pairs, i.e., the slot time ($T_S$), is constant in a block.

In this fixed-block approach, as many blocks are measured and averaged as are required to reach the desired SNR for each excitation frequency in the set (panel).

On the other hand, it is preferred if, when the desired SNR is reached for an excitation frequency f2, the still planned pulse pairs for this excitation frequency f2, and consequently their averagings, are skipped.

It is advantageous in this respect that the measurements continue with the remaining pulse pairs in shortened blocks, i.e., with less slots, which further reduces the measurement period.

It is, moreover, preferred if at least two sets with pulse pairs that are at least partially different with respect to the second excitation frequency f2 are selected, wherein the blocks of the individual sets are presented consecutively, and the DPOAE's are measured and averaged. The sets are thus processed one after the other.

In this flexible-block method with fixed pulse arrangement, seven pulse pairs with different excitation frequencies f2 are arranged, for example, such that approximately the averaging time that is required to reach a certain signal-to-noise ratio is allocated to all of them in accordance with general experience.

Thus, the first set contains about four pulse pairs, even though a total of seven are to be measured. If all seven pulse pairs were combined in a block, the recovery time for each individual frequency would be excessively long, e.g., 6×40 ms=240 ms.

In order to obtain a meaningful compromise between the shortest measurement period and sufficient time for the fading of each DPOAE, several sets are presented one after the other according to the invention, the seven pulse pairs being distributed to the sets, e.g., in such a way that pulse pairs with low excitation frequencies f2 (and therefore also low excitation frequencies f1) occur in several sets.

Because the background noise (1/f noise) increases with excitation frequencies f2 that are too low, this assignment results in the DPOAE's for pulse pairs with lower excitation frequencies f2 being averaged more often than those for higher excitation frequencies f2. This, again, results in a reduced measurement period.

However, if, in a patient, one of the excitation frequencies f2 results in only a very slight DPOAE, such as at f2=3 kHz, averaging must be carried out much longer than usual, despite the good noise background, which is why the other excitation frequencies f2, which are also presented in the measured set, are also stimulated for an unnecessarily long time, which could prolong the measurement period in such situations again.

In a further development, it is therefore preferred that it be checked for each pulse pair continuously whether a desired SNR is reached, and that the pulse pairs for this excitation frequency f2 be eliminated in the further measurement and that the remaining pulse pairs be possibly distributed anew to the sets.

In this flexible-block method with free pulse pair arrangement, the length of the measurements for the individual pulse pairs is no longer defined in relation to one another. Indeed, averaging was also carried out in some of the previously described method variants only until the desired SNR was reached for each excitation frequency f2, but that meant that all pulse pairs had to wait for the last pulse pair, so that all excitation frequencies f2 but one had a higher SNR than required, which is the cost of a measurement period that is too high.

According to the invention, it is therefore now checked continuously for each pulse pair whether the SNR is reached; as soon as this is the case, it is checked whether another pulse pair is not yet completed. In this way, the completely measured pulse pairs are eliminated from the measurement one after the other, and only the remaining pulse pairs continue to be presented.

Wherein now, on the one hand, it is checked whether the octave separation between two consecutive pulse pairs is maintained. If this is no longer the case, the pulse pairs are possibly no longer being processed in the blocks to which they were originally assigned, but in other (newly defined) blocks. It is further checked whether the required time lag T (corresponding to the time for one slot ($T_S$) plus the required fading time ($T_{Abkl.}$)) between two pulse pairs with the same excitation frequency f2 is maintained.

Preferably, the DPOAE is measured and averaged for all excitation frequencies f2 contained in the set or sets at a sound level L2 respectively assigned to the excitation frequency, and at least one new measurement at new sound levels L2 is then performed, wherein the new sound level L2 for each excitation frequency f2 is determined for the respectively new measurement preferably in a threshold value approximation method from the measured DPOAE's.

This method is repeated until a growth curve of measured values of the sound levels of the DPOAE's can be determined for each excitation frequency f2 for 3 to 4 different sound levels L2, from which growth curve the respective threshold values are then determined.

Typically, it is calculated, based upon the first measured DPOAE for each excitation frequency f2, what the next lower sound level L2 should be. If the method was started with an L2 of 45-55 dB SPL, it is highly probable that the following next lower sound level is between 35 to 50 db SPL. If the seven calculated new sound levels maintain the specified condition for the maximum sound level difference between two pulse pairs, the previously used method can be used again in order to determine an average value of the sound level Ldp of the DPOAE's for each growth curve at the location of the new sound level L2.

It is preferred in this regard that the growth curve be determined from at least three values determined at three different sound levels L2, but at the same excitation frequency f2, for the sound level Ldp of the DPOAE's, wherein the at least three sound levels L2 include an upper sound level L2, which is used to determine a lower sound level L2, wherein the third, medium sound level is determined using the upper and the lower sound levels, and that preferably a preliminary lower sound level L2 be determined from the upper sound level L2 and population data, preferably using the formulas (1) to (14) from the subsequent section 2.2.3, and that thereafter the medium sound level L2 be determined from the upper sound level L2 and the preliminary lower sound level, said medium sound level preferably being in the center between the upper and the preliminary lower sound level L2, and that, furthermore, a final lower sound level L2 be determined from the upper sound level L2 and the medium sound level L2, preferably using the formulas (1) to (14).

This iterative method first selects the upper sound level L2, then estimates a lower sound level using population data and the upper sound level, then determines the medium sound level between the upper and the preliminary lower sound levels, and thereafter determines anew, from the upper and the medium sound levels, the lower sound level closest to the threshold level, using the individual slope, which can now be determined.

It is, however, possible that the sound level condition is not fulfilled for one or several excitation frequencies f2. It is, in principle, also possible that the threshold value approximation method leads to the results that a lower sound level L2 is to be set for some excitation frequencies f2, that no DPOAE's could be measured for other excitation frequencies f2, and that, therefore, excitation must now be carried out using a higher sound level L2.

The blocks must then be adjusted accordingly by defining new panels, wherein it can occur that individual measurements must be performed for certain excitation frequencies f2.

If a patient, for example, shows a hearing loss only at 6 kHz, nothing can be measured at a starting level of, for example, 45 dB SPL after the first presentation.

The excitation frequency f2=6 kHz is then not presented in a flexible-block method with fixed pulse arrangement. If all sound levels L2 of the remaining excitation frequencies f2 are processed, up to three individual measurements with a block length of 70 to 120 ms follow, in order to achieve a threshold value determination at f2=6 kHz.

In a flexible-block method with free pulse arrangement, this can, however, be done more flexibly. In this case, pending pulse pairs are continuously checked for their compatibility with respect to the sound level difference and the time lag. It is further checked whether pending pulse pairs can be moved to slot(s) that have become available. In many cases, the number of individual measurements can thereby be reduced.

The new method and the new device can be used commercially in newborn hearing screenings, by pediatricians in well-child checkups, in ENT clinics, and by ENT physicians—namely, respectively to examine the faculty of hearing.

They can also be used by hearing aid acousticians for the adjustment of hearing aids, which can now be carried out, not iteratively, but automatically, and by patients who can perform an automated hearing test at home in order to check, for example, whether they must visit a physician or a clinic, or whether their hearing aid must be adjusted anew.

It is also conceivable to integrate the new device in hearing aids, where they are used in situ for automatically adjusting the hearing aid provided with the device to a change in the hearing of the hearing aid wearer.

Other advantages result from the description and the appended drawing.

It goes without saying that the features mentioned above and the features yet to be explained below can be used not only in the respectively specified combination, but also in other combinations or alone, without departing from the scope of the present invention.

BRIEF DESCRIPTION OF THE DRAWINGS

Exemplary embodiments of the invention are explained in more detail in the following description with reference to the appended drawings. They show.

DETAILED DESCRIPTION OF THE DRAWINGS

Figure 1:
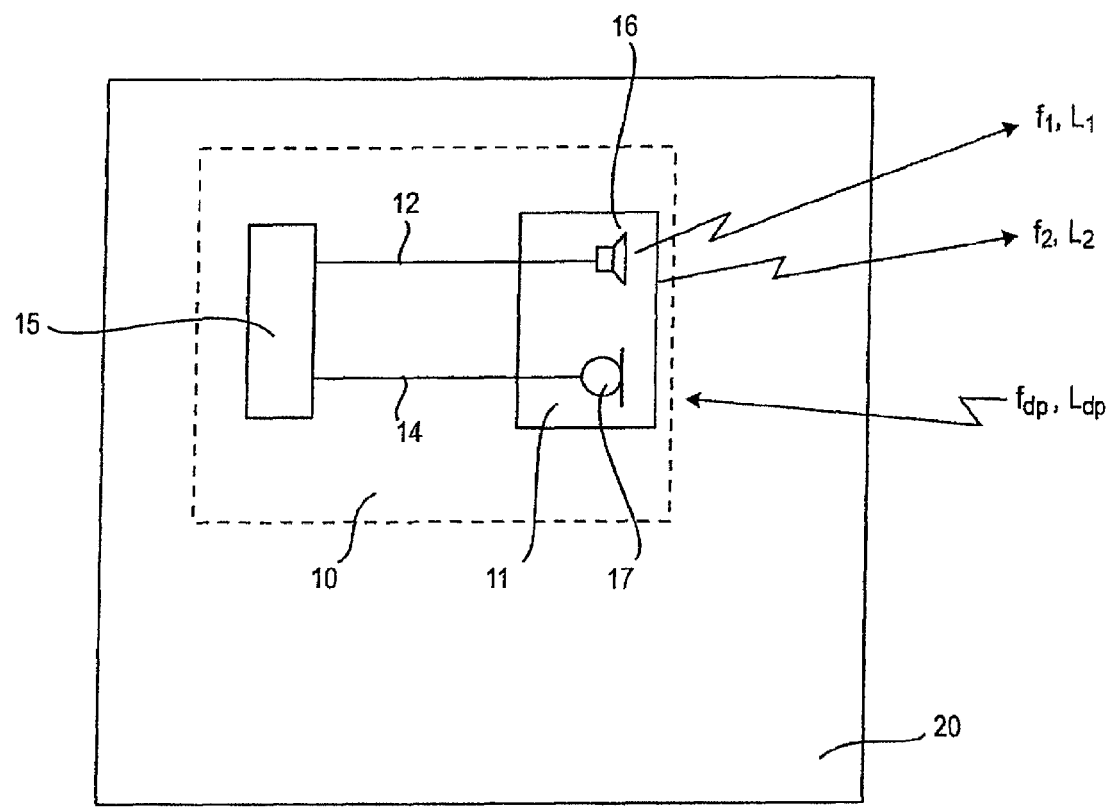
FIG. 1 a basic sketch of a device, with which the new method is performed.

A device 10 to be used according to the invention is shown schematically in FIG. 1; it typically comprises at least one ear probe 11, which is connected to a sound card or another AD card in a computer unit 15—in this case, a computer—via cable 12, 14.

According to DE 199 05 743 A1 mentioned above, a transmission path can be provided between a headphone carrying two ear probes and the computer, in order to avoid disturbing noises that could be caused by the cable. Because of the two ear probes, the measurements can be binaural in this case.

Each ear probe 11 comprises at least one highly linear loudspeaker 16, which emits the two excitation signals f1, L1 and f2, L2, and at least one microphone 17, which measures the DPOAE's, i.e., their sound pressure levels Ldp at a frequency fdp=2 f1−f2, adjusted using f2. Often times, each ear probe 11, however, comprises two loudspeakers 16, so that no technical distortions occur in the stimulation with the two tones f1, f2, said distortions being hard to separate from the physiological DPOAE's.

The computer can be provided externally or integrated into the ear probe 11. The computer is designed to generate the pulse pairs (f1, f2) used according to the invention and to adjust them adaptively during the measurement. It can store the pulse pairs (f1, f2) and the measured DPOAE's (Ldp, fdp) for later analysis, and can make them available to be read.

Alternatively, the computer can also perform the analyses in real time.

The results of the measurement are so-called growth curves for the selected excitation frequencies f2, from which the computer 15 then determines the respective threshold values, which constitute an objective evaluation of the faculty of hearing and can be used for different purposes. It is important in this respect that the new method allow for a very quick determination of the growth curves, which promotes acceptance of the method.

Figure 2:
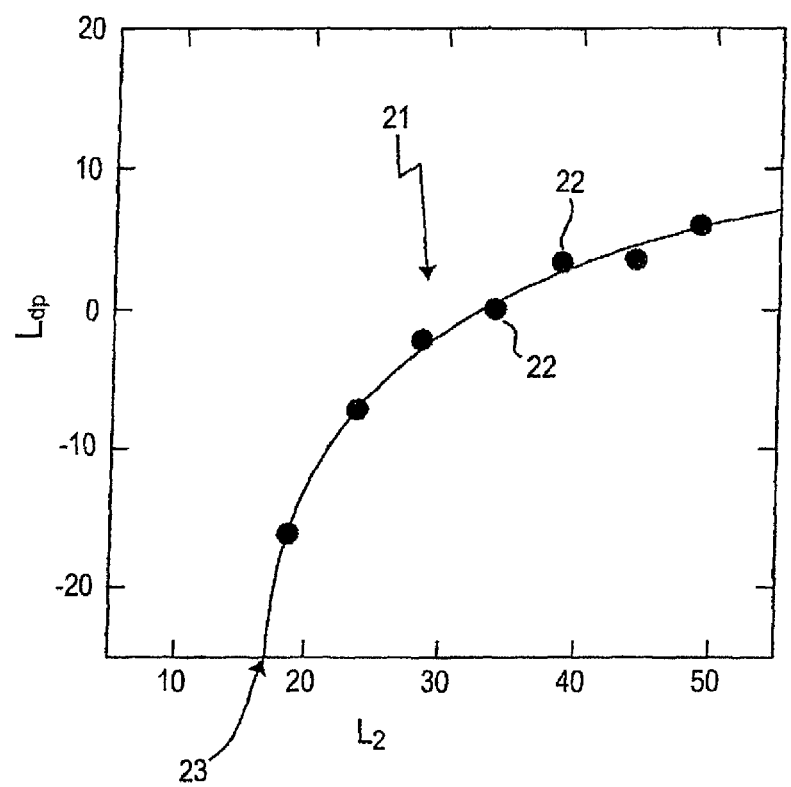
FIG. 2 a basic growth curve as it can be recorded and extrapolated using the new method.

A basic growth curve 21 is shown in FIG. 2. The measured level Ldp of the DPOAE's is plotted for an excitation frequency f2 against the sound level L2. From the seven measured values 22 for the DPOAE's, the threshold value 23 is extrapolated.

For the adjustment of the signals f1, f2 output by the computer to the loudspeaker 16 integrated into the ear probe 11, a final amplifier and/or an impedance adjustment and frequency response correction can be provided, which is realized in the form of a passive or active electronic circuit.

For the adjustment of the electrical signals generated by the microphone 17 to the computer interface, a preamplifier and a frequency response correction can be provided, which is also realized in the form of a passive or active electronic circuit.

If not all processing steps described are performed in the ear probe 11, either a cable connection or a wireless connection is provided. If all processing steps are performed in the ear probe 11, a wireless connection is provided for the transmission of the measurement data to a playback device, either after the measurement or in real time.

The data can also be stored as clinical data in clinical information systems.

The devices 10 described in this respect are used for examining the faculty of hearing by pediatricians, in ENT clinics, by ENT physicians, by hearing aid acousticians, and by patients at home. They can, however, also be integrated directly into hearing aids, in order to adjust them in a way during operation to a change in the hearing of the wearer.

FIG. 1 schematically shows a hearing aid 20, in which the device 10 is arranged.

The method to be performed with these devices was described above in its individual required and preferred steps. Below is a complete overview of preferred exemplary embodiments with, in part, slightly modified nomenclature, which exemplary embodiments are, however, not to be considered as limitations on the extent of protection or the scope of the present invention.

1. Introduction

A time-optimal procedure for measuring DPOAE growth functions must take into account different levels of measured value acquisition and analysis, which are classified as follows:

1.1) Measurement of an Individual DPOAE

This requires determining a minimally-achievable signal-to-noise ratio, determining how the signal and the noise should be calculated, a suitable artifact reduction procedure, and, in general, a maximum measurement time, after which the measurement is to be aborted as unsuccessful.

1.2) Threshold Value Approximation

When measuring growth functions, there is the question of at which excitation levels and in what sequence the single measurement values must be taken, and of how many single measurement values there should be. For the extrapolation procedure, it has been shown that, often, only the three points closest to the threshold of a growth function contribute to the estimation of the extrapolated threshold, and that the accuracy of the estimation increases when other points are omitted. This results in the idea of targeting these three points when conducting measurements, in order to save time on the remaining points.

As will be shown, the measuring point closest to the threshold is the most critical one. If its excitation level is chosen to be too low, either an average over too long a time must be calculated or it can even occur that, after the maximum single measurement time runs out, it cannot be determined with sufficient reliability. If it is too high, the extrapolation error grows, since the last measuring point is located farther from the estimated threshold.

Thus, according to the invention, a procedure is provided, which, based upon a first valid single measuring point that preferably should be the measuring point that is the third and furthest from the threshold, determines both the following measuring points according to optimal criteria, wherein, with each following measuring point, the calculation of the optimal next excitation level shall be adaptively refined.

The question of how the first single measurement value furthest from the threshold should be excited shall be considered separately. Essentially, what is considered here is a global strategy, which can emerge in different ways, depending upon the application.

In general, it is useful to excite the first measurement value at around L2=45 dB SPL, since, above this level, according to the invention, growth functions for normal hearers are already saturated, i.e., they produce values that are not helpful for an optimal threshold estimate. If, for example, newborns were omitted from a sieve test, this would be a good option, because most newborns have normal hearing, and, therefore, the average measurement time for the sieve test would probably be minimized, since, for most of the population, only three single measurement values (per frequency) need to be obtained, and it is rare for the first threshold-furthest measuring point to be attempted without success.

With patients who come to the clinic with hearing loss, growth functions that are appropriate for a normal-hearing population are much less common, while the number of cases whereby the maximum measurement time for a single measurement value is used up at L2=45 dB SPL without obtaining a valid value can already be considerable.

In this area, procedures that newly position a growth function if there is no optimal excitation should also be considered, and so should those that adjust growth functions depending upon the results from other frequencies for multi-frequency measurements (i.e., pulse interleaving procedures with multiple frequencies).

1.3) Temporal Pulse Interleaving Procedure

As a rule, the state of the inner ear should be determined, not at a single frequency, but at a suitable number of frequencies—typically at octave or half-octave intervals in the 1 kHz≤f2≤8 kHz range. This means that multiple growth functions must be measured.

When compared to continuous DPOAE, pulsed DPOAE have the severe drawback that the measurement at a frequency-noise level combination in general has a low duty factor and, therefore, produces a correspondingly low signal-to-noise ratio for the same measurement time.

This drawback, however, is enormously reduced with the invention, in that several measurements are interleaved in the time-frequency space, i.e., they are presented alternately time-delayed. Thus, for example, within a sufficiently often-repeated block, 7 time-delayed frequencies can be stimulated and analyzed.

The simplest implementation is a fixed arrangement of excitation pulses inside a block; this is called a block-fixed procedure. When arranging the pulse pair within a block, the frequency and time sequence must be chosen in way that allows the signals to interfere with each other only within a negligible range.

This procedure functions almost optimally, especially when the noise background and the occurrence of artefacts is similar at all the frequencies used.

Further optimization is achieved when the stimulating pulse pair is arranged, not in a block-fixed, but in a block-flexible way. This leads to additional time-saving in situations where the measurement at one frequency-level combination has already achieved a sufficient signal-to-noise ratio, while another still requires significantly more time.

In this case, in the block-flexible pulse interleaving procedure, before the completion of one of the single measurements currently taking place in the block, one or several pulse pairs that already have achieved the required signalto-noise ratio are replaced with those of another frequency or level, which are still being measured.

For this purpose, a standard rate is produced, which sets the minimum distance in the time-frequency-level space.

In detail:

2.1) Measurement of an Individual DPOAE

Suitable procedures for determining criteria for inclusion of measurement values—here, the DPOAE—in the averaging process, and for determining an average value that returns a preset signal-to-noise ratio (SNR), are sufficiently known from the state of the art; see, for example, Müller and Specht, "Sorted averaging—principle and application to auditory brainstem responses," in Scand. Audiol. 1999, 28: 145-9.

The inventors, however, have determined that the decay time of pulse responses can present a problem, when the measurement time is to be reduced by decreasing the block length.

During typical measurements in the frequency range of around f2=2 kHz, a block length of T=70 ms is sufficient to make sure that the pulse response has already decayed within one block, so that it does not produce any appreciable measuring error due to interference with the pulse response from the repeated simulation by another pulse pair.

This, however, is not true when the frequency of the DPOAE in question (as a rule, fdp=2f1−f2) is close to a spontaneous otoacoustic emission (SOAE).

In order to limit the measuring error produced by these problems, the inventors employ various procedures:

A) Adjusting the block length to the decay time of the pulse under a certain level. This procedure has the drawback that, under certain circumstances, a significant prolongation of the measurement time must be accepted, and that a certain averaging with associated time costs is already necessary to determine the decay time. Thus, the procedure is only useful if the necessary measurement is at a precisely maintained frequency.

B) In the clinical practice, the measurement of a precisely defined frequency is, however, not necessary. In the general view, a sufficient representation of the state of the cochlea can be obtained by measuring frequencies at octave intervals—with higher requirements, at half-octave intervals—thus, for example, at f2=0.75, 1, 1.5, 2, 3, 4, 6, 8 kHz.

In such applications, measuring at an f2 frequency that is within 50-150 Hz of the target frequency might be sufficient. Thus, if the presence of SOAE's needs to be checked, either a) in an a priori measurement, whose assessment will be used to offset the actual f2 frequency of the stimulus to maintain a sufficient safety distance between SOAE's and fdp, or b) when measuring DPOAE's, to be able to recognize the problem with too high decay time at its f2 target frequencies, via an algorithm that is executed during the measurement, with a repetition of the measurement with offset f2 stimulus frequencies, if necessary.

The choice between these two variants can be decided on the probability of occurrence of SOAE's for the given application. If, for application with severely hearing impaired, SOAE's are only rarely to be expected, the time costs can be saved by omitting SOAE's (e.g., hearing screening for older adults); in contrast, with newborns, SOAE's are almost guaranteed to be present, and the probability of their distorting the DPOAE measurement is higher.

For A), an SOAE measurement typically takes 40 s to obtain a noise background of −30 dB SPL at f=2 kHz. The necessary frequency offset can be adjusted, depending upon the strength of the SOAE's found.

For B), the optimized averaging algorithm is to be used. It predicts that when blocks with unusually high noise levels are excluded, the noise follows a clear rule. If it does not, or if, after a certain time, practically every block is excluded, it is a sign that the chosen noise value no longer accords with the assumption of a random, uncorrelated process.

If, for example, the noise figure is related to the amplitude of the envelopment of the time signal immediately before another pulse response is expected, the averaging process can function properly for a certain number of blocks. However, as soon as the noise amplitude drops to the value of the decayed pulse response to the previous stimulus pulse, the amplitude will not be reduced by averaging anymore, if the decaying pulse response is highly reproducible, and, thus, shows a high correlation.

A scheme for the measuring start of a growth function assumes that the measurement begins with a starting level L2 for the second primary tone at f2. The level L1 for the first primary tone f1 is determined for the frequency in question according to a standard curve, e.g., according to the level range as described by P. Kummer et al. in "The level and growth behavior of the 2f1−f2 distortion product otoacoustic emission and its relationship to auditory sensitivity in normal hearing and cochlear hearing loss," in J. Acoust. Soc. Am., 103(6): 3431-3444, 06 1998.

If no DPOAE can be measured, the level L2 of the second primary tone is increased by $\Delta L2$, until the maximum achievable primary tone level is produced. If no DPOAE is found even then, another optimization of the first primary tone level L1 is attempted.

If a DPOAE is measured, the threshold value approximation procedure described below follows.

2.2) Threshold Value Approximation 2.2.1 Determination of the First Measuring Point Since experience with normal hearers shows that the DPOAE growth functions saturate partially relatively early, the first measured value should be picked so that it corresponds with the highest possible excitation level, at which, as a rule, no saturation is to be expected. In the case of a normal hearer, a point thus measured would still be usable and measured without loss of time. It would effectively be the threshold-furthest point of the growth function.

Experience thus far suggests the excitation level of L2=45 dB SPL. If this point is selected to be too low, the number of cases where the maximum permissible measurement time has elapsed without obtaining a usable single measurement value grows.

The strategy can optionally be varied as follows: The maximum permissible measurement time is reduced for the first measuring point. This results in less time being lost, if the DPOAE threshold is above L2. If it is only slightly lower, then, in a later step, when L2 will be measured with a longer measurement time, another attempt at obtaining the same measuring point can be made. This last method uses the advantage of the comparably quickly obtained information of the upper points of the growth function, in order to be able to adjust time-optimally the level of the lowest point of the growth function, whereby the highest time efficiency is achieved.

2.2.2 Determination of the Second Measuring Point

Hereinafter, it will be assumed that there is a measurement of three pulse pairs for a given f2, i.e., of three different noise levels L2, for each second excitation frequency f2. This corresponds to the minimal number of points that can be used in the extrapolation procedure with quality control (determining the correlation coefficients and the standard deviation of the estimated threshold).

The measurements of normal hearers show a high correlation between the slope of the growth function and the amplitude of the DPOAE at an average excitation level—around L2=45 dB SPL. It is thus advisable to choose the second excitation level so that it falls between the first and the third excitation levels. For this purpose, the slope of the growth function is estimated with the help of population average values (see Dalhoff et al., 2013, Hear. Res. Bd. 296, Table 2, p. 77) that are best determined independently of frequency.

The slope can then be used for determining the time-optimal excitation level L2 for the last, threshold-closest measuring point. For this purpose, Section 2.2.3 provides a procedure, which then in equation (2) is used as m for the population average value mentioned above. With the first (threshold-furthest) measuring point and the population data, the threshold-closest (third) measuring point is estimated. The second measuring point is then placed in the middle, between the first and the third point.

2.2.3 Determining the Last Measuring Point at the Lowest L2 Excitation Level

It is assumed that two or more measuring points for a growth function are already available at higher excitation levels L2. In accordance with Section 2.2.2, for example, both the higher measuring points are available, so that now, the third (threshold-closest) measuring point can be determined again—this time, however, with an individually defined slope.

This requires solving the problem of how to choose the last and lowest L2 excitation level that maintains, with the lowest possible time costs, minimal estimation error for the threshold of the growth function in the final extrapolation.

Two questions must be answered for this purpose. First: What influence does the measuring error for the last, threshold-closest measuring point resulting from limited averaging time have on the regression, and thereby, on the estimation error of the extrapolated threshold? It is generally clear here that a measuring point close to the threshold (with the same measuring error) leads to lower extrapolation error. Second: The last point of the growth function must, however, be measured at a certain signal-to-noise ratio in order to be viewed as valid; this means that the closer it is selected to be to the threshold of the growth function, the longer the required averaging time will be. Both these considerations combined produce a conclusive optimality criterion.

The points of the growth function should be numbered from the lowest to the highest excitation level, i.e., opposite to their time order. Next, we search for point $P_1$ with excitation level $x_1$, while points $P_2, \ldots, P_n$ are already available. Based upon the points available, a preliminary regression line (or, at n=3, a connecting line) can be found, with $y(x)=m_{e,n-1}x+b_{e,n-1}$, where e stands for estimated, and n−1 represents the number of points involved in the estimation.

It will be assumed in what follows that y(x) describes the actual growth function without any error, while the additional new measuring point produces a measuring error $N_1$ due to the final averaging time, so that the measured (or estimated from the measurement) value has an amplitude of $y_{1,e}=y_1+N_1$, if $y_1$ is the true amplitude.

The slope of the regression lines based upon the measurement of $P_1$ (which includes error) is calculated with:

$$m_e = \frac{\overline{xy_e} - \overline{x}\,\overline{y_e}}{\overline{x^2} - \overline{x}^2} \quad (1)$$

The line here means that the averaging process is variable.

Therefore:

$$\Delta m = m_e - m = \frac{\overline{xy_e} - \overline{x}\,\overline{y_e}}{\overline{x^2} - \overline{x}^2} - m \quad (2)$$

The intercept is calculated with:

$$b_e = \overline{y}_e - m_e \overline{x} \quad (3)$$

and $\Delta b = b_e - b$ becomes $$\Delta b = \frac{N_1}{n} - \Delta m \overline{x} \quad (4)$$

The extrapolation error $\Delta x_{edpt}$ present due to the measuring error is determined with the quotient rule, provided the error is not too big:

$$\Delta x_{edpt} = \frac{b\Delta m - m\Delta b}{m^2} \quad (5)$$

Therefore:

$$nm\Delta x_{edpt} = N_1 \frac{(x_1 - \overline{x})(\overline{x} - x_{edpt}) - \beta}{\beta} \quad (6)$$

abbreviated:

$$\beta = \overline{x^2} - \overline{x}^2 \quad (7)$$

After separating the required point $x_1$, on the basis of the average value, we find $$N_{1,reg} = \frac{nm\Delta x_{edpt}\left(x_1^2\left(\frac{n-1}{n}\right) - \frac{2\gamma x_1}{n} + \delta - \frac{\gamma^2}{n}\right)}{x_1(x_{edpt}(1-n)+\gamma) + \gamma x_{edpt} + \delta} \quad (8)$$

with $\gamma = \Sigma_2^n x_i$ and $\delta = \Sigma_2^n x_i^2$.

The subscript in $N_{1,reg}$ here represents the acceptable noise for the regression criterion. This equation is used to calculate the permissible noise at point $P_1$, if a maximum extrapolation error $\Delta x_{edpt}$ is provided.

The requirement for the signal-to-noise ratio criterion is:

$$N_{1,snr} = \frac{m(x_1 - x_{edpt})}{SNR} \quad (9)$$

Thus, the signal-to-noise ratio is the linear ratio of the amplitudes. The two requirements for the noise as defined in the equations (8) and (9) allow the required averaging time to be determined, if a noise amplitude density $\tilde{N}$ is known:

$$\tau = \left(\frac{\tilde{N}}{N_1}\right)^2 \quad (10)$$

Since both conditions are to be satisfied simultaneously, the respective longer measuring time must be observed.

Equalizing the two noise criteria results in a quadratic equation with the following solution:

$$x_1 = -\frac{p}{2} - \sqrt{\frac{p^2}{4} - q} \quad (11)$$

with $$p = -\frac{(2\Delta x_{edpt} SNR \gamma + \delta - x_{edpt}^2 (1-n))}{\alpha} \quad (12)$$

$$q = \frac{(\Delta x_{edpt} SNR(n\delta - \gamma) + x_{edpt}(\gamma x_{edpt} + \delta))}{\alpha} \quad (13)$$

$$\alpha = (\Delta x_{edpt} SNR + x_{edpt})(n-1) - \gamma \quad (14)$$

It may be necessary to deviate from the recommendation in practice. It is thus known that the growth function for normal hearing persons no longer follows the ideal linear course in the semi-logarithmic representation below a level of approximately $L_2$=25 dB SPL, since, strictly speaking, there is no distortion product threshold. If an excitation level is recommended in this area due to the process described above, the estimation accuracy is systematically impaired. It is possible to determine, for example, a minimum value for $L_2^{(1)}$.

Alternatively, a set of L2 noise levels can be deposited in the computer in a simplified process, said set to be used for every excitation frequency f2. It is further provided that a separate set of L2 noise levels be deposited for each excitation frequency f2.

2.3) Temporal Pulse Interlacing Procedure
2.3.1 Time-frequency Pulse Interlacing Procedure
2.3.1.1 Rigid Block Time-frequency Pulse Interlacing Procedure We are assuming that a panel with several pulse pairs of different frequencies f1, f2 and levels L1, L2 are presented in a block, and that, nevertheless, so-called ensembles are formed from, for example, 4 such blocks each in PTPV process (see, for example, Zelle et al., "Extraction of otoacoustic distortion product sources using pulse basis functions," in J. Acoust. Soc. Am., 134(1): EL64-EL69, 07 20139), said ensembles allowing the extraction of the time signal of a desired distortion component, e.g., at fdp=2f1−f2.

We call this presentation mode a rigid block mode if the sequence of the pulse within a block is given and/or cannot be modified during the measurement.

One possible approach is a delayed arrangement of different excitation frequencies f2(i), i=1, 2, 3, ... n of n pulse pairs in a block. The block length is selected, for example, to T (and/or $T_B$)=160 ms; the starting times of the pulse pairs are evenly distributed across the block—in this example, with n=4 and f2=1.5; 3; 2; 4 kHz. The main interest is then the extraction of the distortion component at fdp=2f1−f2.

Figure 3:
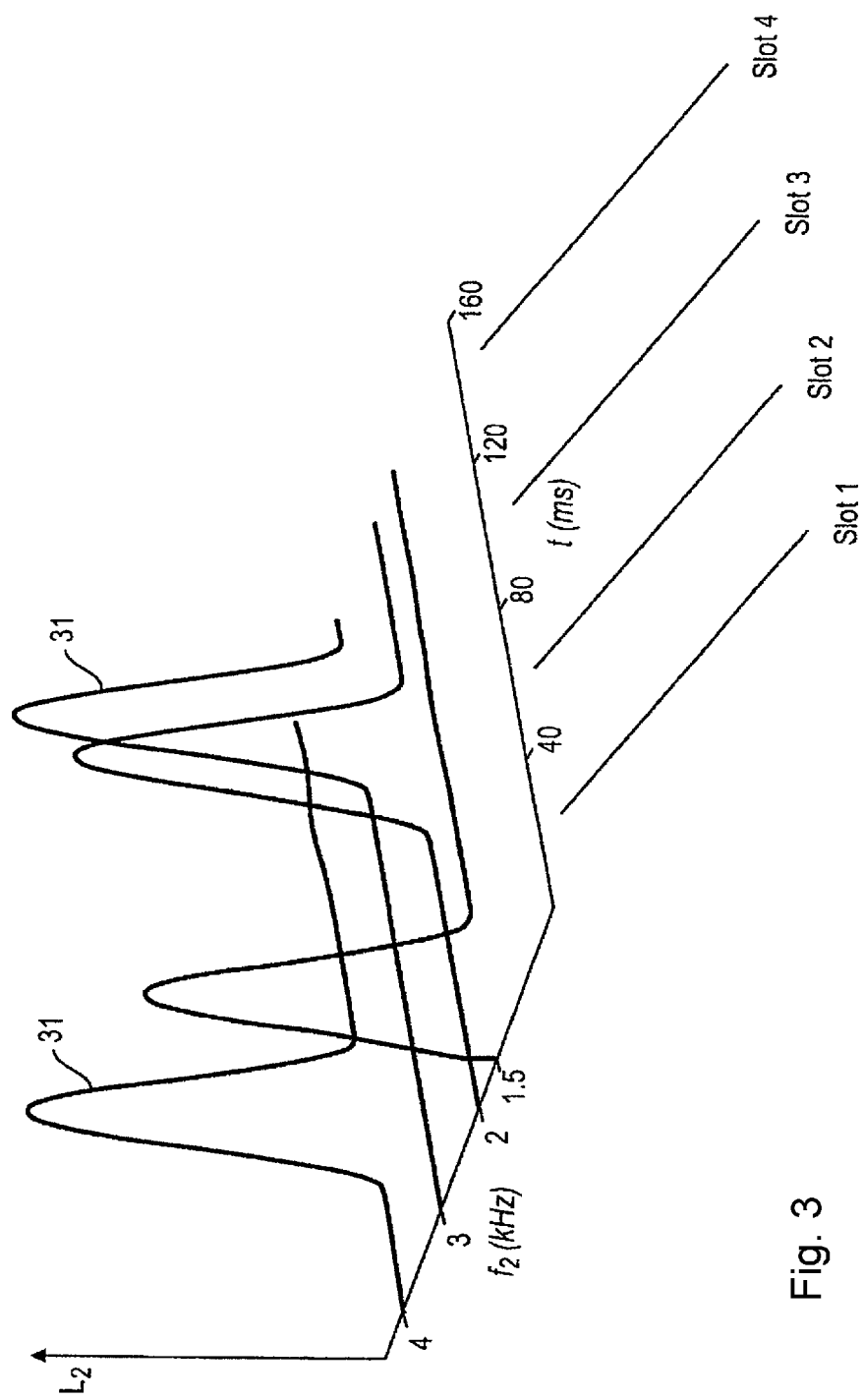
FIG. 3 the envelopes for four different f2 excitation pulses with the frequencies 1.5; 4; 2; 3 kHz for the fixed-block time-frequency pulse combination method with fixed pulse pair arrangement.

FIG. 3 shows the envelopes 31 for four different f2 excitation pulses with the frequencies 1.5; 4; 2; 3 kHz for the rigid block time-frequency pulse interlacing procedures. Those envelopes are used to switch the excitation sounds on or off. The pulse form is represented in this image only by cosine-shaped ramps without a steady state. FIG. 3 shows a snapshot, as it were, of a measuring block for a panel.

Figure 4:
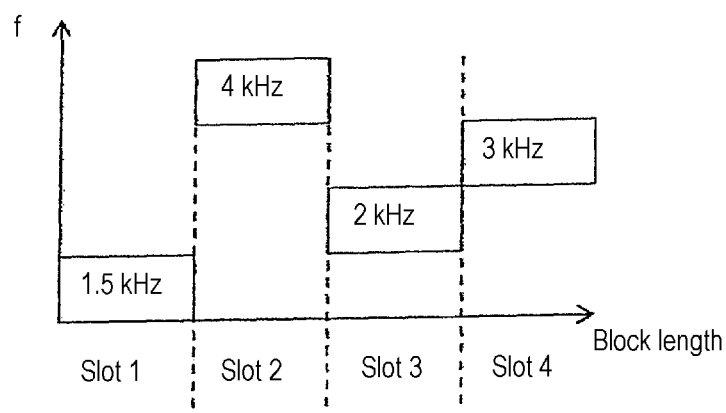
FIG. 4 the distribution of a panel of four f2 pulse pairs to four slots in a block for the fixed-block time-frequency pulse combination method with fixed pulse pair arrangement.

FIG. 4 shows the distribution of the four pulse pairs combined in a Panel A to the four slots of the block.

Figure 3B:
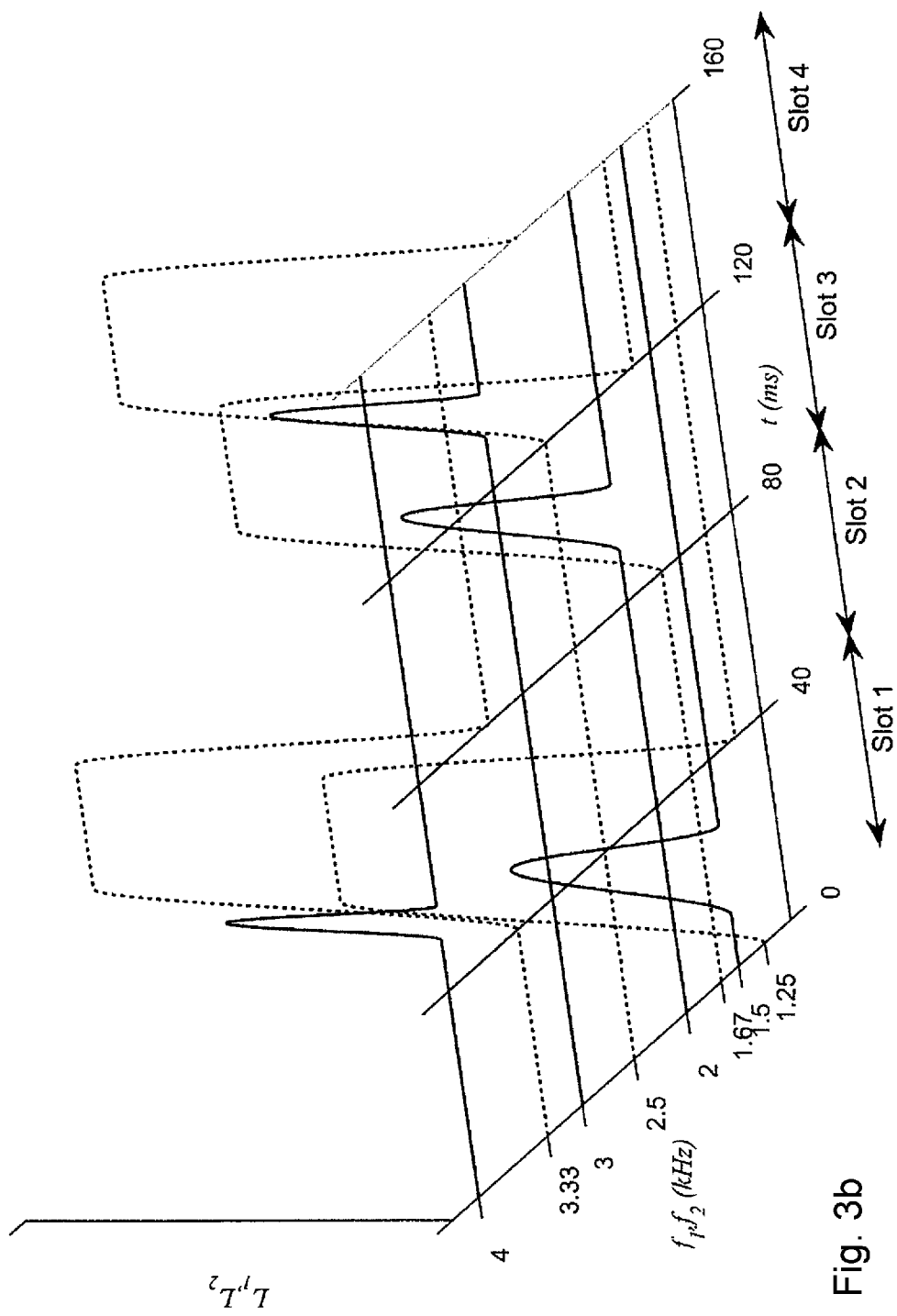
FIG. 3*b* the envelopes for four different pulse pairs with respectively four different excitation frequencies f2 and f1 with the frequencies f1 1.25; 1.67; 2.5; 3.33 kHz and the frequencies f2 1.5; 2; 3; 4 kHz for the fixed-block time-frequency pulse combination method with fixed pulse arrangement.

FIG. 3b shows the envelopes 31 for four different f2 excitation impulses with the frequencies 1.5; 4; 2; 3 kHz, as well as the envelopes 32 for the four different f1 excitation pulses with the frequencies 1.25; 3.33; 1.67; 2.5 kHz corresponding in the pulse pairs for the rigid block time-frequency pulse interlacing procedure. FIG. 3b therefore shows a block with four pulse pairs that are presented in four slots (Slot 1 through Slot 4) of 40 ms duration each. As can be seen, the excitation frequencies f1 of the pulse pairs are switched off at the start of a slot and switched on again at the end of a slot. Due to the slot length and/or the switch-on period of the excitation pulses of the f1 frequencies, these each develop plateaus, as can be seen from their envelopes. The four different f2 excitation frequencies that are presented in four excitation pulses within the four slots are only switched on respectively once the f1 excitation pulses have been switched on. The f1 excitation pulses are only switched off once the f2 excitation pulses have been switched off and have faded. The processes of switching the individual excitation pulses f1 and f2 on and off are represented by cosine-shaped ramps. On the other hand, the plateaus for the f1 pulses do form a steady state that is between the cosine-shaped ramps of the processes of switching on and off. Block time $T_B$ in the depicted block consisting of four pulse pairs f1, f2 is 160 ms, corresponding to the sum of the four slot times $T_S$ (4×40 ms). As shown, the presentation of short f2 pulses (and/or the presentation of short pulses for at least one of the two sounds of the pulse pairs) allows the separation of two signal components in the time signal of the distortion product, which may lead to falsified measuring results, in case of the normal continuous presentation, through interference.

Panel A of the four f2 pulse pairs is presented in a block of 160 ms, in which each f2 pulse pair takes up a slot of 40 ms. This block is repeated until a pre-selected signal-to-noise ratio (here also referred to as SNR) is reached for all four measured DPOAE.

This selection of frequencies and their arrangement is appropriate for two reasons:

A) Masking and Interference

Frequencies in semi-octave steps, i.e., here, for slots i=1; 3 and i=2; 4, are arranged in the block at a maximum distance, since the frequency ratio f2/fdp is approx. 1.5. The consequence is that basically two interferences dominate—in this example, for i=1;3:

I) The presentation of the f2(i=3) pulse can mask the answer fdp(i=1) on the cochlea, if it has not yet faded sufficiently. This, however, applies only to the second source, which is often not in the foreground of the diagnostic procedure.

II) The presentation of the f2(I=3) pulse can mask the f2(I=1) pulse on the cochlea, since they are only a minor third apart. This is also where, usually, the primary contribution to the DPOAE's that is more important for the diagnosis is affected. The time lag of T/2=80 ms here ensures that the interfering and/or masking signal components have usually faded to an acceptable level.

B) Time Needed

In this rigid block process, one has to average until the frequency that delivers the worst signal-to-noise ration and/or the highest artifact ratio has reached the required minimum signal-to-noise ratio. In this example, this is the measurement at f2=1.5 kHz. Its noise background is, however, usually no more than 30% worse than the frequencies f2=2; 3; 4 kHz; so, the time loss is manageable.

Figures 5, 6:
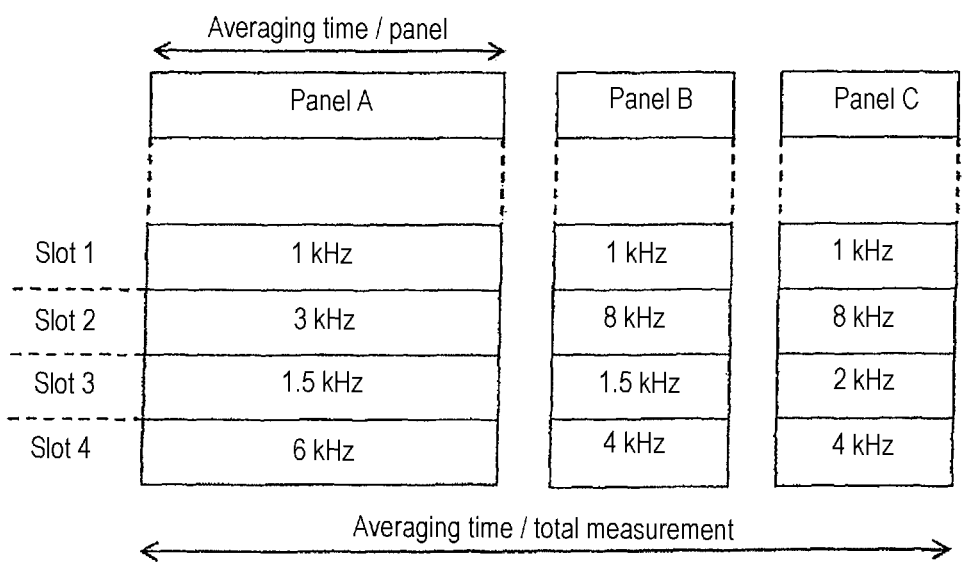
FIG. 5 the distribution of a total of seven f2 pulse pairs to two panels and two blocks with four slots each for the fixed-block time-frequency pulse combination method with fixed pulse pair arrangement.
FIG. 6 the distribution of a total of seven f2 pulse pairs to three panels and three blocks with four slots each for the flexible-block time-frequency pulse combination method with fixed pulse pair arrangement.

FIG. 5 shows the distribution of seven excitation frequencies f2 on two panels A and B in two blocks with four slots of 40 ms each. First, panel A is processed, i.e., for each f2, the average of the noise level Ldp of the respective DPOAE with the desired SNR is determined.

Then, panel B is processed in the same way. The block with panel B also has a block duration of 160 ms each, but could be reduced to 120 ms, since the frequency spacings between the f2 and the fdp are of sufficient size.

2.3.1.2 Flexible Block Time-frequency Pulse Interlacing Procedure with Fixed Pulse Arrangement If the frequency area to be covered has a massive variation in signal-to-noise background or of artifact frequency, and/or if the process is to run perfectly and individually for each patient, the variability with respect to the required averaging time for the respective frequency f2 must be expected to be large.

One solution for this problem is a flexible block method for the arrangement of pulse pairs. The frequencies used are, for example, f2=1; 1.5; 2; 3; 4; 6; 8 kHz. In normal conditions, the measurement at f2=1 kHz shall take four times longer than at f2=2; 3; 4 kHz, since the noise background is doubled, at least if one is aiming for the same noise background.

There are two basic strategies for reacting to this situation. Firstly, one can accept the higher noise background. The consequence of this is that the estimation accuracy is less at lower frequencies, since this noise is taken into consideration over the course of the threshold approximation when the point that is closest to the threshold in the growth function is determined, and a higher extrapolation error is accepted. Secondly, one can try to provide a respectively longer measuring time for the frequency with the increased noise background.

The frequencies are therefore divided into three panels A, B, and C that are each presented in a block with 4 slots: slot 1 permanently presents the pulse pair at f2=1 KHz for all three panels; slot 3 presents the pulse pair for ¾ of the time at f2=1.5 kHz, and the pulse pair at f2=2 kHz for the rest of the time; in slot 2 the pulse pair at f2=3 kHz is presented for the first half of the measuring time and the pulse pair at f2=8 kHz for the second half of the measuring time; and in slot 4 the pulse pair at f2=6 kHz is presented for the first half of the measuring time, and the pulse pair at f2=8 KHz for the second half of the measuring time.

FIG. 6 shows the distribution of the seven f2 pulse pairs on the total of three panels A, B, and C. Once again, the panels A, B, and C are processed consecutively. In panel A, the average values for the Ldp at f2=3 kHz and f2=6 kHz are already determined with sufficient SNR. In panel B, the measurement is continued for f2=1 kHz, completed for f2=1.5 kHz, and started for f2=4 kHz and f2=8 kHz. The measuring time for panel A is greater than the one for panel B. In panel C, the measurement for f2=1 kHz, f2=4 kHz, and f2=8 kHz is completed and recorded and concluded for f2=2 kHz.

In such an arrangement, the various noise and/or artifact conditions for the various excitation frequencies are taken into account. It is ensured that a presentation of an f2(i+1) a semi-octave higher than f2(i) never immediately follows the latter, and, additionally, the total measuring time in slots 2 and 4 is asymmetrically distributed on the three panels so that the higher frequencies, f2=6; 8 kHz have more averaging time assigned to them when the noise background in them rises slightly again.

Here, the first excitation level is processed first, followed by the second excitation level in the same arrangement according to the processing of the threshold approximation, etc.

This flexible block procedure may also work with less than an ideal outcome, especially if the DPOAE's are very diverse, i.e., there is a strong probability of a massive hearing impairment. A higher level for the pulse interlacing procedure can thus only be reached with a free, situation-adapted pulse arrangement.

2.3.1.3 Flexible Block Time-frequency Pulse Interlacing Procedure with Free Pulse Arrangement In this case, jobs are assigned to the measurement of growth functions according to the threshold approximation procedure. If DPOAE's are measured for seven frequencies f2 in semi-octave steps, seven jobs are processed accordingly. It is expedient to conduct the measurements with very similar excitation levels L2, to reduce masking issues. Consequently, all jobs start with the level that would be the one farthest from the threshold for a normal hearing person.

However, those seven jobs are not necessarily started simultaneously. Rather, measurement starts with panel A. Panels B through D have not been determined yet; they are the result of the automatically conducted new allocation of a slot once the computer unit 15 has determined that a respective DPOAE for a pulse pair measured in panel A has a sufficient SNR.

Figure 7:
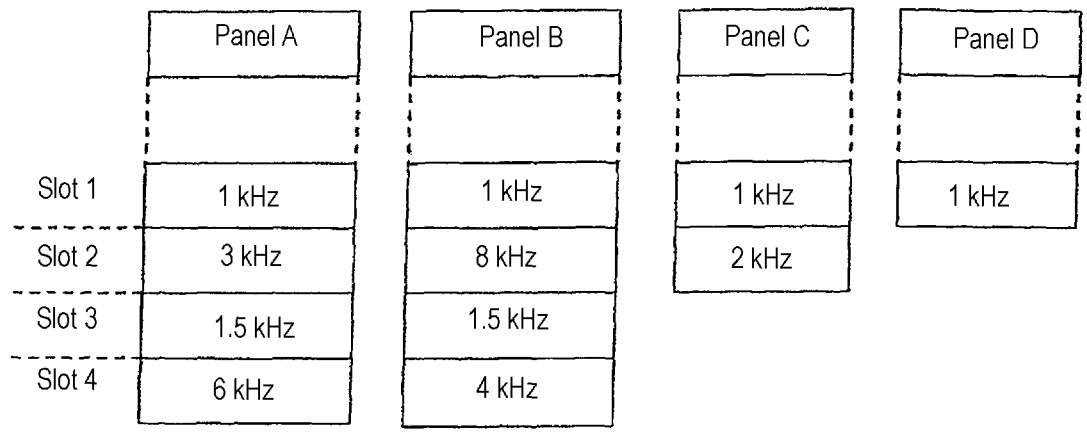
FIG. 7 the distribution of a total of seven f2 pulse pairs to four panels and four blocks with a variable number of slots for the flexible-block time-frequency pulse combination method with free pulse pair arrangement, under the simplified assumption that the measurement periods for the selected f2 pulse pairs are uniform.
Figure 8:
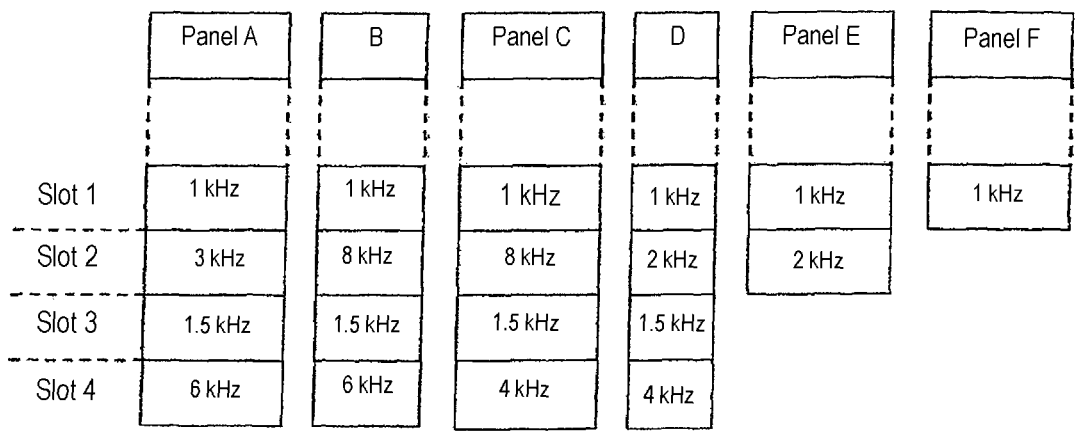
FIG. 8 the distribution of a total of seven f2 pulse pairs to six panels and six blocks with a variable number of slots for the flexible-block time-frequency pulse combination method with free pulse pair arrangement, without the simplified assumption that the measurement periods for the selected f2 pulse pairs are uniform.

FIGS. 7 and 8 show an exemplary representation of how the new allocation takes place. The jobs are distributed to four panels A, B, C, and D with up to four slots in a block, according to FIG. 7. The current arrangement of jobs—i.e., pulse pairs of different f2—in the four slots is referred to as a panel and has to correspond to a set of criteria that, for example, take masking effects into consideration.

Estimated runtimes are entered into a matrix for the slots. When the measurement starts (panel A), the estimated values are based upon empirical data of the population that dominates in terms of diagnostic tasks. All jobs are monitored during the presentation of the individual blocks. As soon as a job has reached its termination criteria (sufficient SNR or reaching the maximum presentation time), the estimated processing times for the slots are recalculated, and the freed slot is reallocated to a pulse pair that has yet to be processed.

In the example, the start setting consists of the same arrangement as given above in 2.3.1.2, but is subsequently varied. For the start setting, it was assumed that measurements at f2=1 kHz require four times as much time as those at f2≥2 kHz due to the double noise level, and those at f2=1.5 kHz still require twice the time.

Then, the selected arrangement is almost ideal; theoretically, time is wasted in panel C, since the measurement would finish early, at 2 kHz. The change from panel B and C is crucial. Here, the number of slots was reduced to two, since the required distance of one octave is maintained for the two remaining frequencies so that the double number of pulses per time can be presented, compared to a 4-slot system. Alternatively, the same measuring time may be obtained, theoretically, by applying a consistent 2-slot system.

If it becomes obvious after processing jobs 2 and 7 (f2=3 and/or 8 kHz) that they are clearly earlier, or that the jobs in the remaining slots are running with a delay, a check is conducted to see whether an as yet unprocessed job can be accepted. In this case, this could be job 3 (f2=2 kHz). If, however, it is processed, only job 1 remains in the end, so that, probably, no time can be saved. However, as soon as the jobs in slot 4 are also finished early, the switch to the 2-slot system can occur at an earlier point in time, and the measurement can be completed with an individual measurement at 1 kHz once job 3 (f2=2 kHz) has been processed.

While the distribution of a total of seven f2 pulse pairs to four panels and four blocks with a variable number of slots under the simplified assumption of uniform measuring times for selected f2 pulse pairs is shown in FIG. 7 for the flexible block time-frequency pulse interlacing procedure with free pulse pair arrangement, FIG. 8 shows a modification in which no uniform measuring times are provided.

As soon as a slot is freed because the average value of the Ldp was determined with sufficient SNR for the f2 measured there until that point, it is allocated to a new f2, resulting in a new panel. This may result in a reduced measuring time for the individual panels. This particularly applies to hearing-impaired patients, since the new procedure does not require any a priori assumptions regarding the expected SNR and/or the required measuring times of the respective DPOAE's.

The invention claimed is:

1. A method for the examination of the hearing ability for at least one ear of a mammal, the method comprising the steps;
providing at least one ear probe on or in the ear, the at least one ear probe including one or two miniature loudspeakers designed for et emitting excitations signals and one receiver configured to capture and forward distortion product optoacoustic emissions (DPOAE's) evoked by the excitation signals;
providing a computer unit that is operably connected to the at least one ear probe;
generating, by the computer unit, a set of at least two different pulse pairs in a measurement block, each pulse pair in the set being presented in a slot having a length T, the slots occurring sequentially without overlapping, the block being a sum of all the slots, the block having a block time being defined by a product of the length of the slot T and a total number of the pulse pairs in the set, a pulse being an on-and-off process within the slot, each pulse pair having a first pulse of a first excitation signal and a second pulse of a second excitation signal, the first excitation signal having a first excitation frequency f1 and a first signal level L1, the second excitation signal having a second excitation frequency f2 and a second signal level L2, the at least two different pulse pairs in the set each having different second excitation frequencies f2, the set being repeated several times in a measuring period containing more than one block;
presenting in the ear the pulse pairs of the first and second excitation signals one pulse pair at a time, and capturing and evaluating the DPOAE's evoked by pairs of excitation signals for different second excitation frequencies;
outputting growth curves on the basis of the measurement DPOAE's evoked;
whereby the outputted growth curves is used as basis for evaluating the hearing ability and diagnosing hearing conditions.

2. A method according to claim 1, wherein a duration of the first and the second pulses in a pulse pair is 2 to 20 ms.

3. A method according to claim 1 wherein the length of the slot T is >10 ms.

4. A method according to claim 1, wherein, in one block, the second excitation frequencies f2 of two immediately consecutive pulse pairs are at least one octave apart.

5. A method according to claim 1, wherein measured signal levels of the DPOAE's for pulse pairs of the same second excitation frequencies f2 are averaged during a measuring period.

6. A method according to claim 1, wherein a start of a first and a consecutive pulse pair with the same excitation frequency f2 have a time lag of 30 to 100 ms.

7. A t method according to claim 1, wherein, at a beginning of the measurements, a check occurs to determine whether the frequency fdp of one of the DPOAE's interferes with a spontaneous emission (SOAE).

8. A method according to claim 1, wherein, within one block, the second signal levels L2 of the pulse pairs have a level difference from one another that is smaller than 15 dB.

9. A method according to claim 1, wherein a sequence of the pulse pairs and a time lag between two immediately consecutive pulse pairs in a block remains constant.

10. A method according to claim 5, wherein, once a desired signal-to-noise ratio for an excitation frequency f2 has been reached, further averages planned for this excitation frequency f2 are skipped.

11. A method according to claim 1, wherein at least two sets of pulse pairs are generated that are at least partially different in terms of the second excitation frequency f2, each set presented as one block, wherein the blocks are presented in chronological sequence.

12. A method according to claim 11, wherein it is continually checked for each pulse pair whether a desired signal-to-noise ratio has been reached and that the pulse pairs for that excitation frequency f2 are eliminated with a further measurement, and the remaining pulse pairs are, if required, redistributed to the blocks.

13. A method according to claim 11, wherein pending pulse pairs are continually checked as to their compatibility with regard to noise level and time lag, and it is further checked whether pending pulse pairs in a block may be re-allocated to freed slots.

14. A method according to claim 1, wherein the noise levels of the DPOAE's for all the second excitation frequencies f2 contained in the or every set are measured and averaged for a second noise level L2 respectively allocated to the excitation frequency f2, and the measurements are conducted at least once for new noise levels L2.

15. A method according to claim 14. wherein for each excitation frequency f2, a growth curve of measured values of the signal levels of the DPOAE's is determined for various signal levels L2, and respective threshold values are then determined from said growth curves.

16. A method according to claim 15, wherein the growth curve is determined from at least three values for the signal level Ldp of the DPOAE determined at three different signal levels L2, but the same excitation frequency f2, wherein the at least three signal levels L2 include an upper signal level L2 that is used to determine a lower signal level L2, wherein the third, middle signal level is determined by means of the upper and the lower signal levels.

17. A method according to claim 16, wherein a preliminary lower noise level L2 is determined from the upper signal level L2 and population data, and then the middle signal level L2 is determined from the upper signal level L2 and the preliminary lower signal level, said middle signal level being in the middle between the upper and the preliminary lower signal levels L2.

18. A method according to claim 16, wherein a final lower signal level L2 is determined from the upper signal level L2 and the middle signal level L2.

19. A device for the examination of the hearing ability for at least one ear of a mammal, comprising:
at least one ear probe configured to be placed on/in the ear, the at least one ear probe including one or two miniature loudspeakers and one receiver wherein the one or every miniature loudspeaker is designed for the presentation of a first excitation signal with a first excitation frequency f1 and a first signal level L1 and/or a second excitation signal with a second excitation frequency f2 and a second signal level L2, and wherein the receiver is designed for the capture and forwarding of a DPOAE's evoked by the first and second excitation signal; and a computer unit operable connected to the at least one ear probe, the computer unit configured to present a set of at least two pulse pairs in a block, each pulse pair having a first pulse of the first excitation signal and a second pulse of the second excitation signal, the at least two pulse pairs in the set having different second excitation frequencies f2, each pulse pair in the set occurring in a slot having a length T, the slot following a preceding slot sequentially without overlapping, the block being a sum of all the slots, the block having a block time defined by a product of the length of the slot T and a total number of the pulse pairs in the set, a pulse being an on-and-off process within the slot, the computer unit further configured such that said set is run repeatedly several times for one measuring period containing more than one block, the computer unit further configured to determine and output growth curves on the basis of the measurement of DPOAE's evoked by pairs of excitation signals for different second excitation frequencies used for evaluation of the hearing ability and diagnosis of hearing conditions.

20. A hearing aid comprising a device according to claim 19.

21. The method according to claim 1, wherein a ratio of f2/f1 is constant.

22. The method according to claim 1, wherein the pulse pair signals do not use the entire time of the slot.

23. The method according to claim 1, wherein the first pulse and the second pulse in a pulse pair are presented at a temporal offset.

* * * * *

UNITED STATES PATENT AND TRADEMARK OFFICE
CERTIFICATE OF CORRECTION

PATENT NO. : 10,561,347 B2
APPLICATION NO. : 15/320474
DATED : February 18, 2020
INVENTOR(S) : Ernst Dalhoff et al.

It is certified that error appears in the above-identified patent and that said Letters Patent is hereby corrected as shown below:

In the Claims

Column 23, Line 23: Remove "et"; and

Column 23, Line 25: Replace "optoacoustic" with --otoacoustic--.

Signed and Sealed this
Nineteenth Day of May, 2020

Andrei Iancu
*Director of the United States Patent and Trademark Office*